United States Patent
Chuang et al.

(10) Patent No.: US 9,903,963 B2
(45) Date of Patent: Feb. 27, 2018

(54) METHOD, APPARATUS AND SYSTEM OF THE CORRECTION OF ENERGY CROSSTALK IN DUAL-ISOTOPES SIMULTANEOUS ACQUISITION

(71) Applicant: NATIONAL TSING HUA UNIVERSITY, Hsinchu (TW)

(72) Inventors: Keh-Shih Chuang, Hsinchu (TW); Hsin-Hon Lin, Changhua County (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 208 days.

(21) Appl. No.: 15/089,722

(22) Filed: Apr. 4, 2016

(65) Prior Publication Data

US 2017/0090050 A1   Mar. 30, 2017

(30) Foreign Application Priority Data

Sep. 25, 2015   (TW) .............................. 104131795 A

(51) Int. Cl.
| | |
|---|---|
| G01T 1/164 | (2006.01) |
| G01T 7/00 | (2006.01) |
| A61B 6/03 | (2006.01) |

(52) U.S. Cl.
CPC .............. G01T 7/005 (2013.01); A61B 6/037 (2013.01); G01T 1/164 (2013.01); G01T 1/1647 (2013.01)

(58) Field of Classification Search
CPC ........ G01T 1/164; G01T 1/1647; G01T 7/005
USPC ..................................................... 250/363.04
See application file for complete search history.

(56) References Cited

U.S. PATENT DOCUMENTS

2014/0341453 A1* 11/2014 Hsu ...................... A61B 6/5264
                                                             382/131

FOREIGN PATENT DOCUMENTS

| TW | 200831939 A | 8/2008 |
|---|---|---|
| TW | 201041559 A1 | 12/2010 |
| WO | WO 2014/012182 A1 | 1/2014 |

* cited by examiner

Primary Examiner — David Porta
Assistant Examiner — Meenakshi Sahu
(74) Attorney, Agent, or Firm — Li & Cai Intellectual Property (USA) Office

(57) ABSTRACT

The present invention relates the system of the correction of energy crosstalk in dual-isotopes simultaneous acquisition (DISA), the system includes a collimator, a metal thin film, a detecting unit, an analyzing unit and a display unit for analyzing energy distribution charts of the dual-isotopes, and using specific equations or artificial neural network methods or independent component analysis to compare the energy distribution charts which are with and without metal thin film The invention uses the metal thin film to remove the energy contamination from dual-isotopes simultaneous acquisition whose photopeak energies are close, the invention effectively separates the energy distribution charts without energy crosstalk, therefore, the system improves diagnostic imaging and relieves patient's discomfort.

10 Claims, 7 Drawing Sheets

METHOD, APPARATUS AND SYSTEM OF THE CORRECTION OF ENERGY CROSSTALK IN DUAL-ISOTOPES SIMULTANEOUS ACQUISITION

BACKGROUND

1. Technical Field

The present disclosure relates to a method, apparatus and system of the correction of energy crosstalk in dual-isotopes simultaneous acquisition, in particular, analyzing sinograms with and without the metal thin film to realize the method, apparatus and system of the correction of energy crosstalk in dual-isotopes simultaneous acquisition.

2. Description of Related Art

FIG. 1 shows the energy distribution chart of Technetium-99m (Tc-99m) and fluorine-18 (F-18). Tc-99m and F-18 has energy crosstalk in the range of 100~200 (keV). So Tc-99m and F-18 should be measured separately in order to enhance the accuracy of diagnostic imaging in the past. However, images taken at different time may suffer misregistration due to the setup error or involuntary motion of the patients.

SUMMARY

An exemplary embodiment of the present disclosure provides a method for correction of energy crosstalk in dual-isotopes simultaneous acquisition, applied when a Single-photon emission computed tomography (SPECT) device scans the dual-isotopes, comprising: scanning the dual-isotopes by the SPECT device, afterwards the SPECT generating energy distribution charts, wherein the SPECT comprises at least one collimator; attaching a metal thin film to a partial area of an inner or outer side of the collimator; comparing and calculating the energy distribution charts having the metal thin film and without the metal thin film, further analyzing the energy crosstalk in the dual-isotopes in order to remove energy contamination from the dual-isotopes simultaneous acquisition for image reconstruction without the energy crosstalk.

An exemplary embodiment of the present disclosure provides a method for correction of energy crosstalk in dual-isotopes simultaneous acquisition, applied when a SPECT device scans the dual-isotopes, wherein Artificial Neural Networks (ANNs) or Independent Components Analysis (ICA) are used to compare and calculate the energy distribution charts having the metal thin film and without the metal thin film, further analyzing the energy crosstalk in the dual-isotopes in order to remove energy contamination from the dual-isotopes simultaneous acquisition for image reconstruction without the energy crosstalk.

An exemplary embodiment of the present disclosure provides a device for correction of energy crosstalk in dual-isotopes simultaneous acquisition, applied when a Single-photon emission computed tomography (SPECT) device scans the dual-isotopes, comprising: a metal thin film; at least one collimator, attached to a partial area of an inner or outer side of the collimator; a detecting unit, measuring energy distribution charts of the dual-isotopes; and a analyzing unit, coupled to the detecting unit for analyzing the energy distribution charts of the dual-isotopes.

An exemplary embodiment of the present disclosure provides a system for correction of energy crosstalk in dual-isotopes simultaneous acquisition, applied when a Single-photon emission computed tomography (SPECT) system scans the dual-isotopes, comprising: a metal thin film; at least one collimator, attached to a partial area of an inner or outer side of the collimator; a detecting unit, measuring energy distribution charts of the dual-isotopes; an analyzing unit, coupled to the detecting unit for analyzing the energy distribution charts of the dual-isotopes; and a display unit, coupled to the analyzing unit for displaying the energy distribution charts of the dual-isotopes; wherein the analyzing unit compares and calculates the energy distribution charts having the metal thin film and without the metal thin film, further analyzing the energy crosstalk in the dual-isotopes in order to remove energy contamination from the dual-isotopes simultaneous acquisition for image reconstruction without the energy crosstalk.

In order to further understand the techniques, means and effects of the present disclosure, the following detailed descriptions and appended drawings are hereby referred to, such that, and through which, the purposes, features and aspects of the present disclosure can be thoroughly and concretely appreciated; however, the appended drawings are merely provided for reference and illustration, without any intention to be used for limiting the present disclosure.

DESCRIPTION OF THE EXEMPLARY EMBODIMENTS

Figure 1:
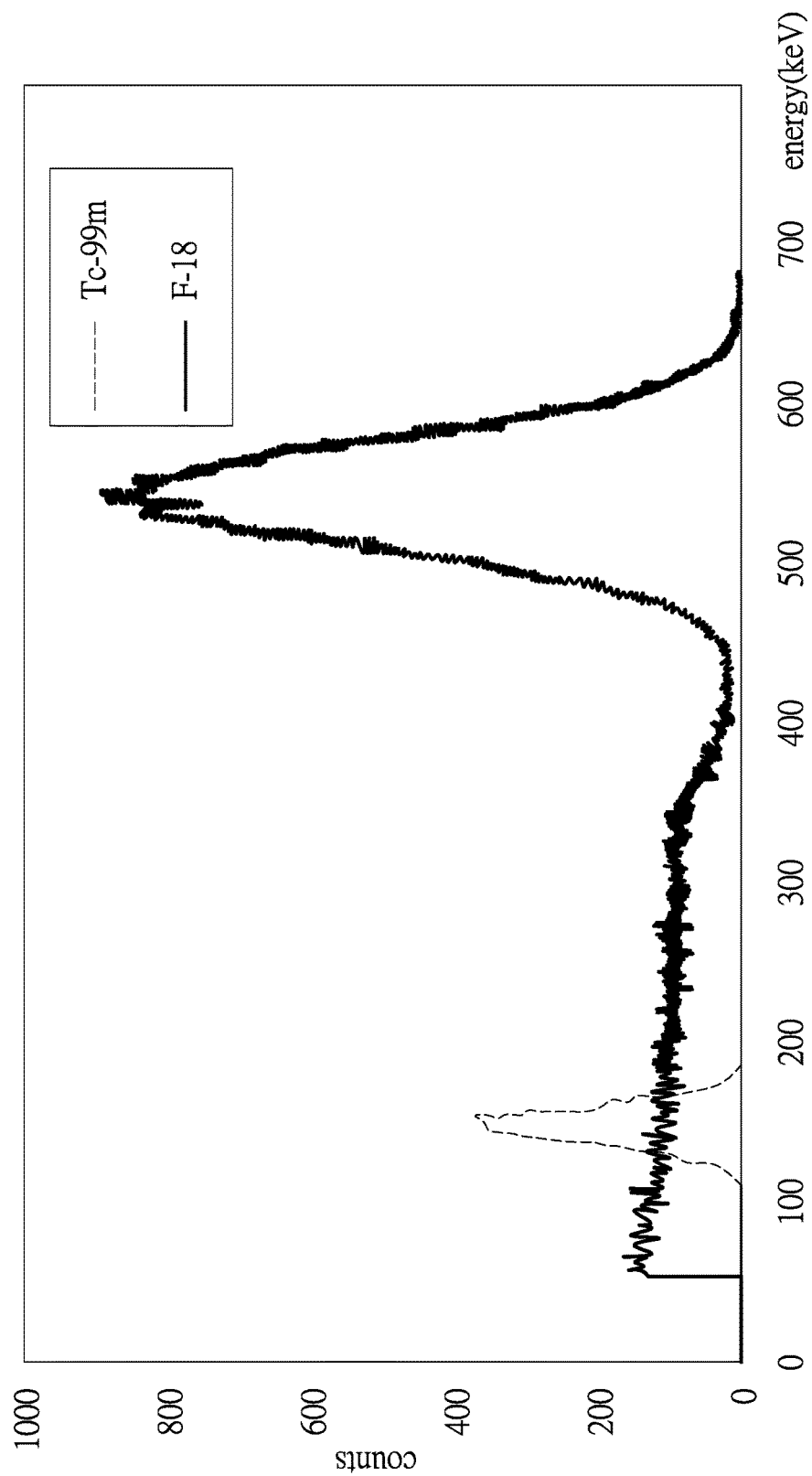
FIG. 1 shows an energy distribution chart of Technetium-99m (Tc-99m) and fluorine-18 (F-18)
Figure 2A:
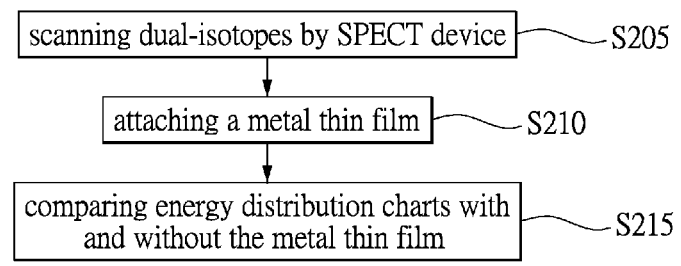
FIG. 2A shows a method of a Single-photon emission computed tomography (SPECT) device to scan dual-isotopes in one embodiment of the present invention.

FIG. 2A shows a method of a Single-photon emission computed tomography (SPECT) device to scan dual-isotopes in one embodiment of the present invention.

According to one embodiment in the disclosure of the present invention, for the method of correction of energy crosstalk in dual-isotopes simultaneous acquisition, applied when the SPECT device scans the dual-isotopes, scanning the dual-isotopes by the SPECT device so as to generate energy distribution charts (S205), wherein the SPECT comprises at least one collimator; attaching a metal thin film to a partial area of an inner or outer side of the collimator (S210), further analyzing the energy distribution charts having the metal thin film and without the metal thin film in order to remove energy contamination from the dual-isotopes simultaneous acquisition for reconstructing the energy distribution charts without the energy crosstalk (S215).

Figure 2B:
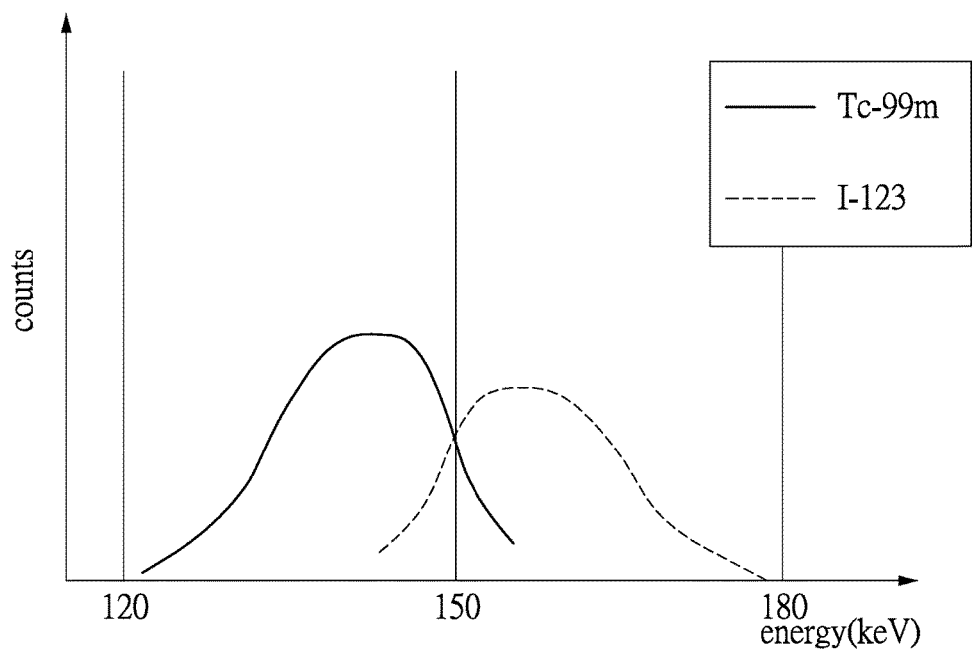
FIG. 2B shows an energy distribution chart of Technetium-99m (Tc-99m) and Iodine-123 (I-123) without the metal thin film in one embodiment of the present invention.
Figure 2C:
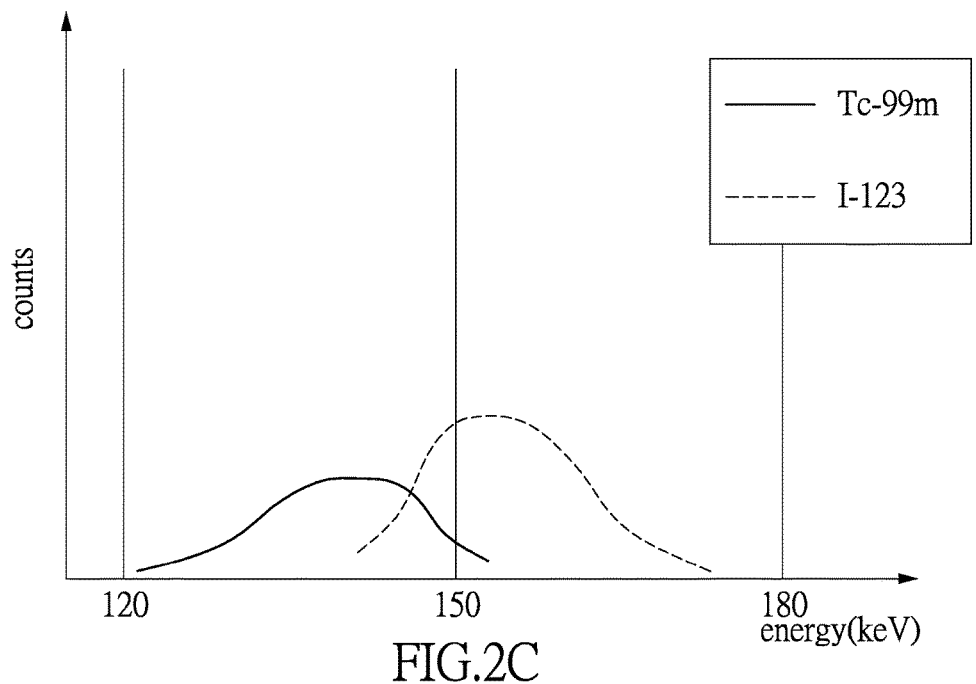
FIG. 2C shows an energy distribution chart of Technetium-99m (Tc-99m) and Iodine-123 (I-123) having the metal thin film in one embodiment of the present invention.

FIG. 2B shows an energy distribution chart of Technetium-99m (Tc-99m) and Iodine-123 (I-123) without the metal thin film in one embodiment of the present invention. FIG. 2C shows an energy distribution chart of Tc-99m and I-123 having the metal thin film in one embodiment of the present invention. The energy distribution chart of Tc-99m and I-123 in the range of 120-180 (keV) has high energy crosstalk, so it is hard to remove the energy contamination of the dual-isotopes consisting of Tc-99m and I-123 in the past.

In one embodiment, the dual-isotope may be selected from Tc-99m, I-123, Iodine-124 (I-124), Iodine-125 (I-125), Iodine-131 (I-131), Indium-111 (In-111), Thallium-201 (Tl-201) and Gallium-67 (Ga-67). In this embodiment, the dual-isotopes consisted of Tc-99m and I-123, and the present invention discloses how to remove the energy crosstalk of Tc-99m and I-123, however, the present is not limited to the selection of the dual-isotopes consisting of Tc-99m and I-123.

In one embodiment, as shown in FIG. 2A, the SPECT device scans the dual-isotopes consisting of Tc-99m and I-123, the SPECT device comprises at least one collimator, the collimator lets the light travel in straight lines in order to reduce optical interference. After the collimator is attached to the metal thin film, each of the dual-isotope may have different attenuation in accordance with the material of the metal thin film. The present invention utilizes the difference of attenuation of the dual-isotope and specific equation to remove energy crosstalk for reconstructing original energy distribution chart. The metal thin film may be attached to an inner or outer side of the collimator, to further explain, the metal thin film may be attached to a partial area or overall area of the metal thin film What's more, the metal thin film is attached to an inner or outer side of the collimator doesn't affect the accuracy of experiment. Last, comparing the energy distribution with and without the metal thin film to analyze the energy crosstalk of the dual-isotope, further reconstructing the original energy distribution chart of Tc-99m and In-123.

Further, the metal thin film is selected from lead (Pb), aurum (Au), argentum (Ag), copper (Cu), platinum (Pt) and tungsten (W). The material of the metal thin film is selected from a high atomic number because the photoelectric effect is prominent for photons with energies from a few electron volts to over 1 MeV in elements with the high atomic number. Wherein the thickness of the metal thin film is 0.05 mm~1 mm, and the thickness and the material of the metal thin film are determined based on the dual-isotope. Specially, the ideal condition was that the metal thin film was selected from 0.25 mm Au.

More, the present invention utilizes equation A, equation B and equation C to reconstruct the energy distribution chart without energy crosstalk, the equation A calculates the total photon number detected in window A and window B without the metal thin film, the equation B calculates the total photon number detected in both window A and B with the metal thin film, and the equation C is used to reconstruct the original photon number without energy contamination. Wherein the energy distribution chart without the metal thin film is calculated by equation A, the equation A is:

$$P_A = f_A + yf_B$$

$$P_B = f_B + xf_A$$

wherein the energy distribution chart having the metal thin film is calculated by equation B, the equation B is:

$$P_{A'} = af_A + ybf_B$$

$$P_{B'} = df_B + cxf_A$$

wherein the energy distribution chart without the energy contamination is calculated by equation C, the equation C is:

$$f_A = \frac{P_{A'} - bP_A}{a - b}$$

$$f_B = \frac{P_{B'} - cP_B}{d - c}$$

Wherein $f_A$ represents photon number of an isotope A detected in an energy window A without the metal thin film, and $yf_B$ represents partial photon number of an isotope B detected in the energy window A without the metal thin film, y represents fraction of the isotope B detected in the energy window A without the metal thin film, $P_A$ represents the total photon number detected in the energy window A without the metal thin film.

Wherein $f_B$ represents the photon number of the isotope B detected in an energy window B without the metal thin film, and $xf_A$ represents partial photon number of the isotope A detected in the energy window B without the metal thin film, x represents the fraction of isotope A detected in the energy window B without the metal thin film, $P_B$ represents the total photon number detected in the energy window B without the metal thin film.

Wherein $af_A$ represents partial photon number of the isotope A detected in the energy window A having the metal thin film, a represents attenuation fraction of the isotope A detected in the energy window A having the metal thin film, and $ybf_B$ represents partial photon number of the isotope B detected in the energy window A having the metal thin film, b represents attenuation fraction of the isotope B detected in the energy window A having the metal thin film, $P_{A'}$ represents the total photon number detected in the energy window A having the metal thin film Wherein $df_B$ represents partial photon number of the isotope B detected in the energy window B having the metal thin film, d represents attenuation fraction of the isotope B detected in the energy window B having the metal thin film, and $cxf_A$ represents partial photon number of the isotope A detected in the energy window B having the metal thin film, c represents attenuation fraction of the isotope A detected in the energy window B having the metal thin film, $P_{B'}$ represents the total photon number detected in the energy window B having the metal thin film The equation A, the equation B and the equation C are used to reconstruct the photon number of the isotope A to an original condition in the energy window A and to construct the photon number of the isotope B to an original condition in the energy window B. Wherein the attenuation fraction a, b, c, and d can be calculated by:

$$a = \frac{P_{A'}[^{123}I]}{P_A[^{123}I]}$$

$$b = \frac{P_{A'}[^{99m}Tc]}{P_A[^{99m}Tc]}$$

$$c = \frac{P_{B'}[^{123}I]}{P_B[^{123}I]}$$

$$d = \frac{P_{B'}[^{99m}Tc]}{P_B[^{99m}Tc]}$$

The present invention may also utilize Artificial Neural Networks (ANNs) or Independent Components Analysis (ICA) to compare and calculate the energy distribution charts having the metal thin film and without the metal thin film, further analyzing the energy crosstalk in the dual-isotopes in order to remove energy contamination from the dual-isotopes simultaneous acquisition for reconstructing the energy distribution charts without the energy crosstalk. ANNs are used to mimic the data processing method of a Biological Neural Network by software or hardware, using nonlinear transfer function to analyze a large amount of data from history events for solving problems. ANNs may be Back Propagation Neural Network (BPNN)—Radial Basis Function Networks (RBFN)—Self-Organizing Map Neural Network (SOMNN) or Recurrent Neural Network (RNN), the present invention is not limited to the type of ANNs. ICA is a computational method for separating a multivariate signal into additive subcomponents. ICA is done by assuming that the subcomponents are non-Gaussian signals and statistically independent from each other.

Figure 3:
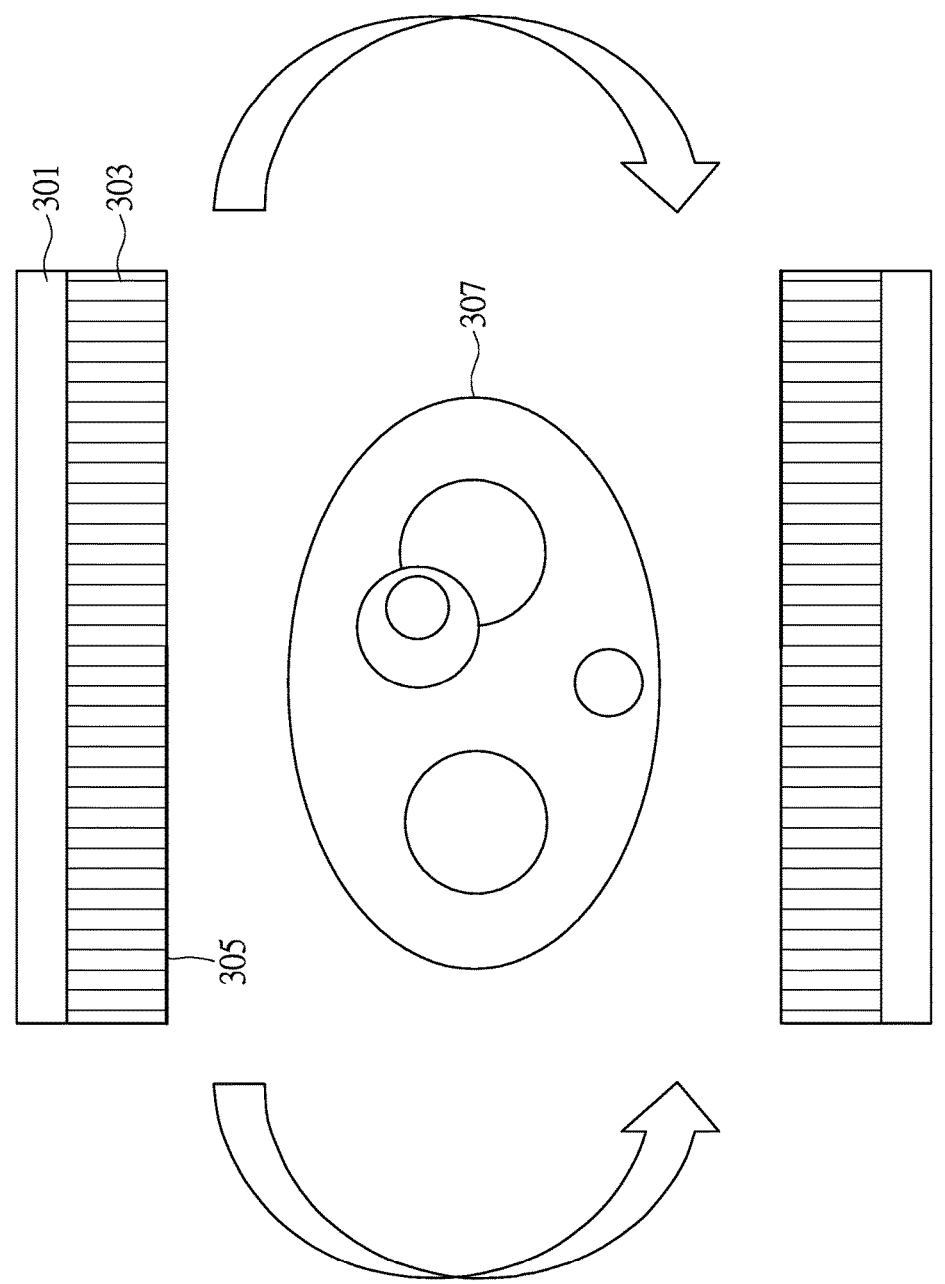
FIG. 3 shows a Single-photon emission computed tomography (SPECT) device includes two collimators to scan dual-isotopes in one embodiment of the present invention.

Next, FIG. 3 shows a Single-photon emission computed tomography (SPECT) device including two collimators to scan dual-isotopes in one embodiment of the present invention. The SPECT device comprises a detector 301, two collimators 303, a metal thin film 305 and dual-isotopes 307. The dual-isotopes are set between each of the collimators 303. The metal thin film 305 is attached to half of the area of each collimator 303. The detector 301 is set in the outer side of the collimator 303 for emitting lights to measure the energy distribution chart of the dual-isotopes 307, and the detector 301 rotates around the dual-isotopes 307 to reconstruct the energy distribution chart without energy contamination by the equation A, equation B and equation C.

Figure 4:
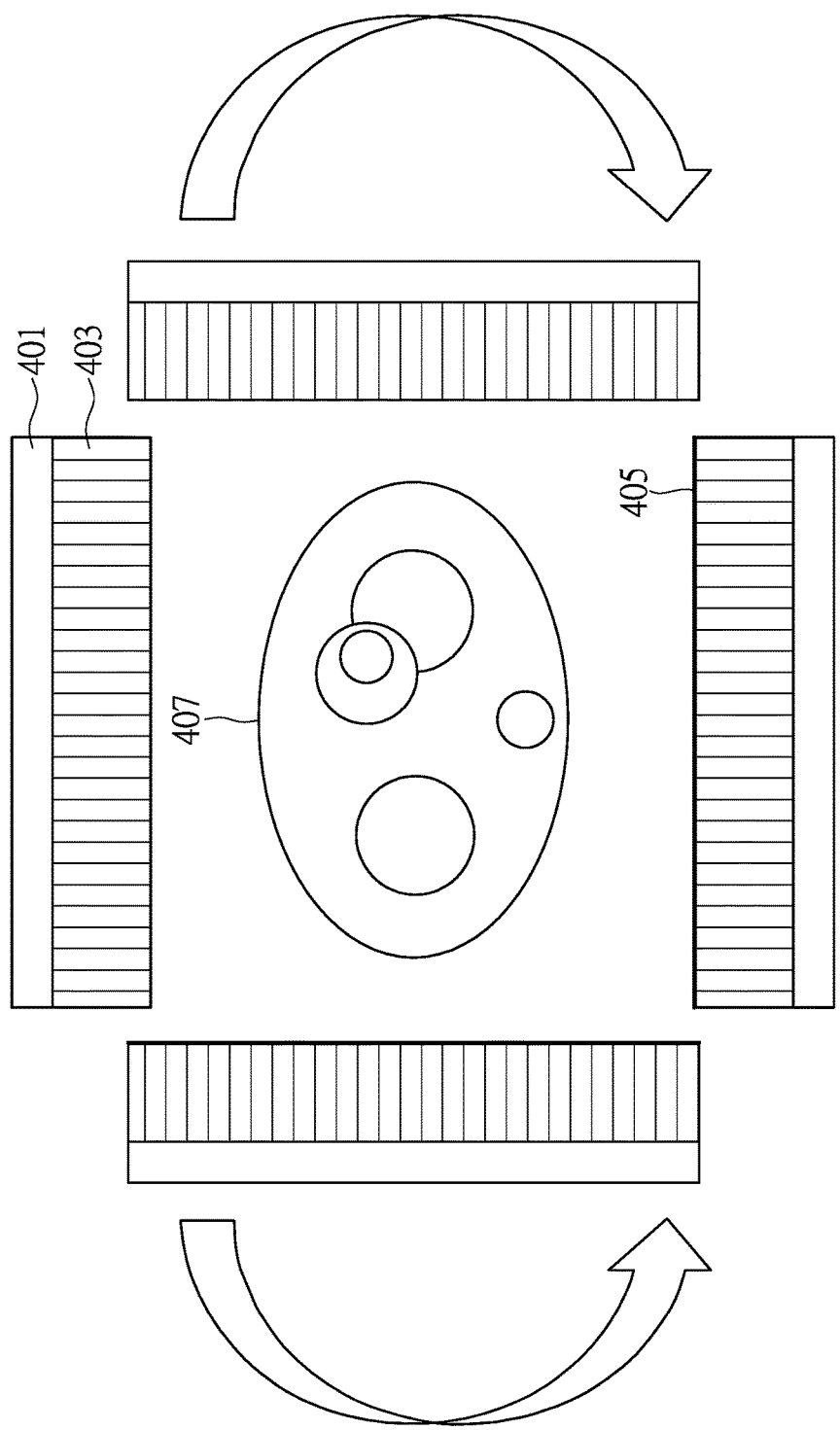
FIG. 4 shows a SPECT device includes four collimators to scan dual-isotopes in one embodiment of the present invention.

FIG. 4 shows a SPECT device including four collimators to scan dual-isotopes in one embodiment of the present invention. To elaborate, using two collimators and four collimators to measure the energy distribution of the dual-isotopes are similar technical means, in order to remove energy crosstalk by comparing the energy distribution chart with and without the metal thin film.

In addition, the SPECT device in FIG. 4 comprises a detector 401, four collimators 403, a metal thin film 405 and dual-isotoes 407. The dual-isotopes 407 are in the middle of the collimator 403. Wherein the metal thin film 405 is attached to overall area of two of the four collimators 403. The detector 401 is set in the outer side of the collimator 403 for emitting lights to measure the energy distribution chart of the dual-isotopes 407, and the detector 401 rotates around the dual-isotopes 407 to reconstruct the energy distribution chart without energy contamination by the equation A, equation B and equation C.

Figure 5:
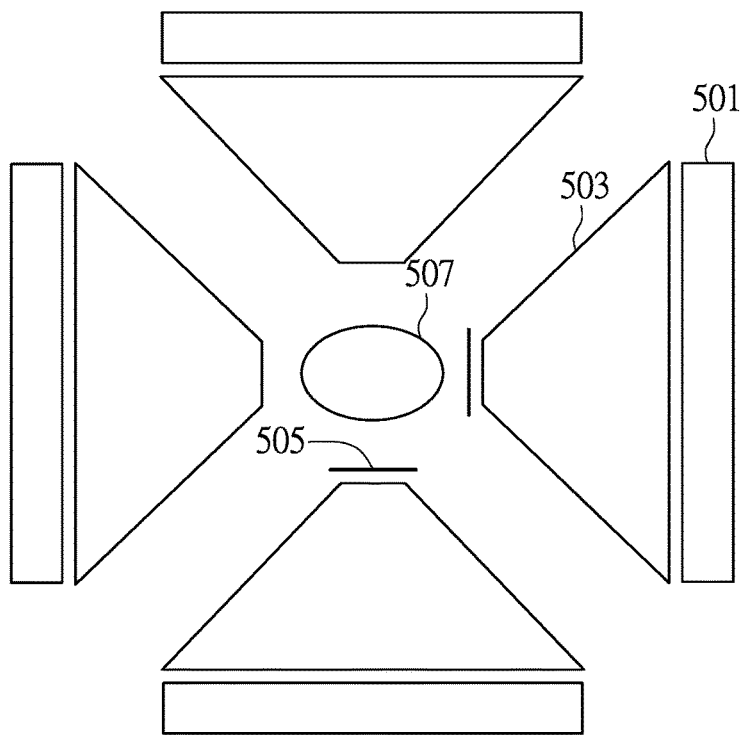
FIG. 5 shows a SPECT device includes pinhole collimators to scan dual-isotopes in one embodiment of the present invention.

FIG. 5 schematically shows a SPECT device includes pinhole collimators to scan dual-isotopes in one embodiment of the present invention. The SPECT device in FIG. 5 comprises a detector 501, four pinhole collimators 503, a metal thin film 505 and dual-isotopes 507. The dual-isotopes 507 are set in the middle of the four pinhole collimators 503. Wherein the metal thin film 505 is attached to overall area of half of the four pinhole collimators 503. The detector 501 is set in the outer side of the four pinhole collimators 503 for emitting lights to measure the energy distribution chart of the dual-isotopes 507. In addition, the pinhole collimator is suitable for measuring lower energy isotope. The side view of the pinhole collimator is ladder-shaped, and the metal thin film 505 is attached to the shorter side of the pinhole collimator 503. Then, the detector 501 rotates around the dual-isotopes 507 to measure the energy distribution chart without energy contamination by the equation A, equation B and equation C.

Figure 6:
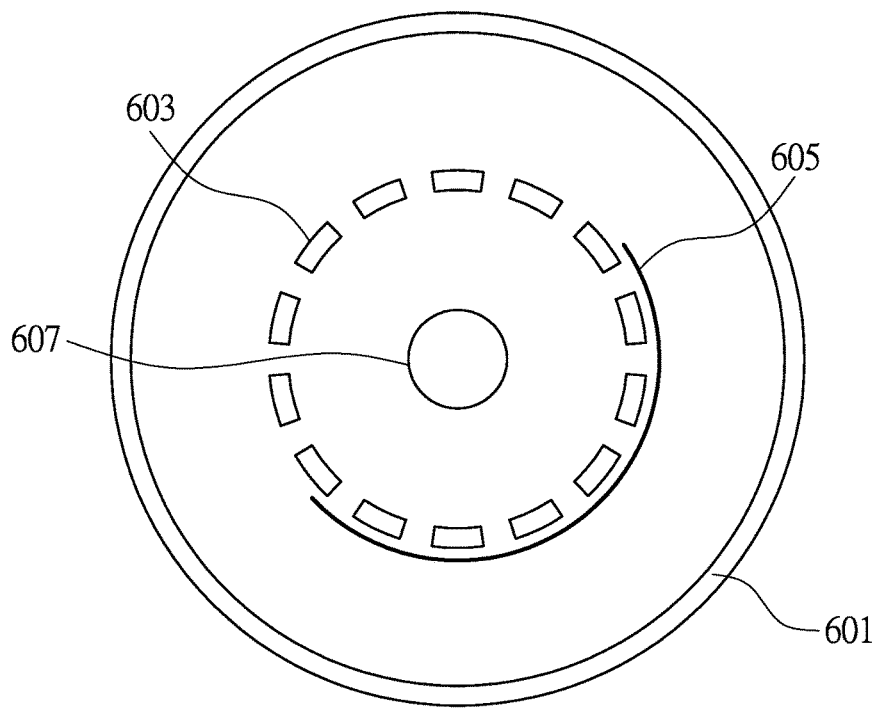
FIG. 6 shows a SPECT device includes rotating collimators to scan dual-isotopes in one embodiment of the present invention.

FIG. 6 shows a SPECT device includes rotating collimators to scan dual-isotopes in one embodiment of the present invention. The SPECT device comprises a plurality of detectors 601, a plurality of collimators 603, a plurality of metal thin films 605 and dual-isotopes 607. The side view of the detectors 601 and the metal thin films 605 form a ring-shaped circle, to further elaborate, the detectors 601 and the collimators 603 is a concentric circle, and the dual-isotopes 607 are on the center point. Besides, the detectors 601 are set in the outer side of the collimators 603 to measure the energy distribution chart of the dual-isotopes 607. The metal thin film 605 may be attached to half of the area of the ring-shaped circle of the collimators 603, in other words, the metal thin films 605 may be attached to left semicircle or right semicircle of the collimators 603. Alternatively, the metal thin film 605 may also be attached to half of the area of the collimator 603 at regular intervals.

Figure 7:
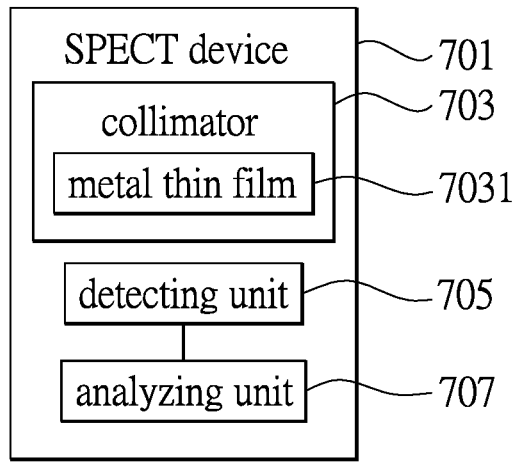
FIG. 7 shows a block diagram of a SPECT device for correction of energy crosstalk in dual-isotopes simultaneous acquisition.

FIG. 7 shows a block diagram of a SPECT device for correction of energy crosstalk in dual-isotopes simultaneous acquisition. The SPECT device 701 comprises a collimator 703, a metal thin film 7031, a detecting unit 705 and an analyzing unit 707, wherein the metal thin film 7031 is attached to a partial area of an inner or outer side of the collimator 703 so as to compare the energy distribution charts with or without the metal thin film 7031. The detecting unit 705 emits lights through the collimator 703 to measure the energy distribution charts of the dual-isotopes. The analyzing unit 707 is coupled to the detecting unit 705 for analyzing the energy distribution charts of the dual-isotopes in order to remove the energy crosstalk by the above-mentioned equation A, B, C, ANNs or ICA.

Figure 8:
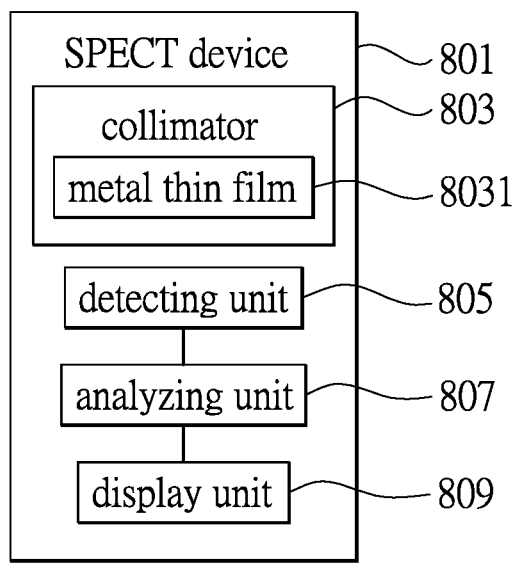
FIG. 8 shows a block diagram of a SPECT system for correction of energy crosstalk in dual-isotopes simultaneous acquisition.

FIG. 8 shows a block diagram of a SPECT system for correction of energy crosstalk in dual-isotopes simultaneous acquisition. The SPECT system 801 comprises a collimator 803, a metal thin film 8031, a detecting unit 805, an analyzing unit 807 and a display unit 809, wherein the metal thin film 8031 is attached to a partial area of an inner orouter side of the collimator 803 so as to compare the energy distribution charts with or without the metal thin film 8031. The detecting unit 805 emits lights through the collimator 803 to measure the energy distribution charts of the dual-isotopes. The analyzing unit 807 is coupled to the detecting unit 805, and the display unit 809 analyzes the energy distribution charts of the dual-isotopes in order to remove the energy crosstalk by the above-mentioned equation A, B, C, ANNs or ICA, and afterwards, the display unit 809 shows the original energy distribution chart without energy contamination.

Thus, disclosure in accordance with present invention is related to a method, apparatus and system for analyzing the energy distribution chart with and without the metal thin film to rize the correction of energy crosstalk in DISA. Further, the material of the metal thin film is selected from a high atomic number because photoelectric effect requires photons in the high atomic number. Utilizing the equation A, B, C, ANNs or ICA to eliminate the energy crosstalk in order to reconstruct the original energy distribution chart, in the above-mentioned embodiment, the energy distribution chart of Tc-99m and I-123 has high energy crosstalk, so it is easier to remove the energy contamination of the dual-isotopes having lower energy crosstalk. The present invention effectively improves diagnostic imaging and relieves patient's discomfort.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. A method for correction of energy crosstalk in dual-isotopes simultaneous acquisition, applied when a Single-photon emission computed tomography (SPECT) device scans the dual-isotopes, comprises:
    scanning the dual-isotopes by the SPECT device, afterwards the SPECT generating energy distribution charts, wherein the SPECT comprises at least one collimator;
    attaching a metal thin film to a partial area of an inner or outer side of the collimator;
    comparing and calculating the energy distribution charts having the metal thin film and without the metal thin film, further analyzing the energy crosstalk in the dual-isotopes in order to remove energy contamination from the dual-isotopes simultaneous acquisition for reconstructing the energy distribution charts without the energy crosstalk.

2. The method according to claim 1, wherein the energy distribution chart without the metal thin film is calculated by equation A, the equation A is:

$$P_A = f_A + yf_B$$

$$P_B = f_B + xf_A$$

wherein $f_A$ represents photon number of a isotope A detected in an energy window A, and $yf_B$ represents partial photon number of an isotope B detected in the energy window A, y represents fraction of the isotope B detected in the energy window A without the metal thin film, $P_A$ represents the total photon number in the energy window A without the metal thin film;
wherein $f_B$ represents the photon number of the isotope B detected in an energy window B, and $xf_A$ represents partial photon number of the isotope A detected in energy window B, x represents the fraction of isotope A detected in energy window B without the metal thin film, $P_B$ represents the total photon number in the energy window B without the metal thin film;
wherein the energy distribution chart having the metal thin film is calculated by equation B, the equation B is:

$$P_{A'} = af_A + ybf_B$$

$$P_{B'} = df_B + cxf_A$$

wherein $af_A$ represents partial photon number of the isotope A detected in the energy window A having the metal thin film, a represents attenuation fraction of isotope A in the energy window A having the metal thin film, and $ybf_B$ represents partial photon number of the isotope B detected in the energy window A having the metal thin film, b represents attenuation fraction of the isotope B in the energy window A having the metal thin film, $P_{A'}$ represents the total photon number in the energy window A having the metal thin film;

$$P_{A'} = af_A + ybf_B$$

$$P_{B'} = df_B + cxf_A$$

wherein $df_B$ represents partial photon number of the isotope B detected in the energy window B having the metal thin film, d represents attenuation fraction of isotope B in the energy window B having the metal thin film, and $cxf_A$ represents partial photon number of the isotope A detected in the energy window B having the metal thin film, c represents attenuation fraction of the isotope A in the energy window B having the metal thin film, $P_{B'}$ represents the total photon number in the energy window B having the metal thin film;
wherein the equation A and the equation B are used to reconstruct the photon number of the isotope A to an original condition in the energy window A and to construct the photon number of the isotope B to an original condition in the energy window B.

3. The method according to claim 1, wherein the dual-isotopes are selected from Technetium-99m (Tc-99m), Iodine-123 (I-123), Iodine-124 (I-124), Iodine-125 (I-125), Iodine-131(I-131), Indium-111 (In-111), Thallium-201 (Tl-201) and Gallium-67 (Ga-67).

4. The method according to claim 3, wherein the metal thin film is selected from lead (Pb), aurum (Au), argentum (Ag), copper (Cu), platinum (Pt) and tungsten (W).

5. The method according to claim 4, wherein thickness of the metal thin film is 0.05 mm~1 mm, and the thickness and the material of the metal thin film are determined based on the dual-isotopes.

6. The method according to claim 1, wherein the SPECT device includes two collimators, the metal thin film is attached to half of the area of each collimator.

7. The method according to claim 1, wherein the SPECT device includes four collimators, the metal thin film is attached to overall area of half of the four collimators.

8. A method for correction of energy crosstalk in dual-isotopes simultaneous acquisition, applied when a Single-photon emission computed tomography (SPECT) device scans the dual-isotopes, therein Artificial Neural Networks (ANNs) or Independent Components Analysis (ICA) is used to compare and calculate the energy distribution charts having the metal thin film and without the metal thin film, further analyzing the energy crosstalk in the dual-isotopes in order to remove energy contamination from the dual-isotopes simultaneous acquisition for reconstructing the energy distribution charts without the energy crosstalk.

9. A device for correction of energy crosstalk in dual-isotopes simultaneous acquisition, applied when a Single-photon emission computed tomography (SPECT) device scans the dual-isotopes, comprises:
    a metal thin film;
    at least one collimator, the metal thin film is attached to a partial area of an inner or outer side of the collimator;
    a detecting unit, measuring energy distribution charts of the dual-isotopes; and
    an analyzing unit, coupled to the detecting unit for analyzing the energy distribution charts of the dual-isotopes;
    wherein the analyzing unit compares and calculates the energy distribution charts having the metal thin film and without the metal thin film, further analyzing the energy crosstalk in the dual-isotopes in order to remove energy contamination from the dual-isotopes simultaneous acquisition for reconstructing the energy distribution chart without the energy crosstalk.

10. A system for correction of energy crosstalk in dual-isotopes simultaneous acquisition, applied when a Single-photon emission computed tomography (SPECT) system scans the dual-isotopes, comprises:
- a metal thin film;
- at least one collimator, the metal thin film is attached to a partial area of an inner or outer side of the collimator;
- a detecting unit, measuring energy distribution charts of the dual-isotopes;
- an analyzing unit, coupled to the detecting unit for analyzing the energy distribution charts of the dual-isotopes; and
- a display unit, coupled to the analyzing unit for displaying the energy distribution chart of the dual-isotopes;
- wherein the analyzing unit compares and calculates the energy distribution charts having the metal thin film and without the metal thin film, further analyzing the energy crosstalk in the dual-isotopes in order to remove energy contamination from the dual-isotopes simultaneous acquisition for reconstructing the energy distribution chart without the energy crosstalk.

\* \* \* \* \*